United States Patent [19]

Gericke et al.

[11] 4,243,810

[45] Jan. 6, 1981

[54] PYRIDONE-ACETIC ACID DERIVATIVE

[75] Inventors: Rolf Gericke; Werner Rogalski; Rolf Bergmann, all of Darmstadt; Walter Hameister, Berlin; Helmut Wahlig, Darmstadt, all of Fed. Rep. of Germany

[73] Assignee: Merck Patent Gesellschaft mit beschrankter Haftung, Darmstadt, Fed. Rep. of Germany

[21] Appl. No.: 8,893

[22] Filed: Feb. 1, 1979

Related U.S. Application Data

[63] Continuation-in-part of Ser. No. 503,705, Sep. 6, 1974, Pat. No. 4,153,693.

[30] Foreign Application Priority Data

Sep. 8, 1973 [DE] Fed. Rep. of Germany ....... 2345402

[51] Int. Cl.³ .......................................... C07D 213/78
[52] U.S. Cl. .................................................. 546/295
[58] Field of Search ......................................... 546/295

[56] References Cited

PUBLICATIONS

Chemical Abstracts, vol. 84, No. 25, item No. 180,071q, Jun. 21, 1976.
Liebigs Annalen der Chemie & Pharmazie, vol. 494, p. 294 (1932).

Primary Examiner—Alan L. Rotman
Attorney, Agent, or Firm—Millen & White

[57] ABSTRACT

Novel pyridone-acetic acid derivative, viz. 3,5-dichloro-4-pyridone-1-acetic acid (I) is used as an intermediate in the production of certain cephem derivatives having anti-bacterial activity against gram-negative and gram-positive bacteria. The acid (I) is prepared by methods generally known in the art, e.g. by reacting 3,5-dichloro-4-pyridone with chloracetic acid or bromoacetic acid.

1 Claim, No Drawings

PYRIDONE-ACETIC ACID DERIVATIVE

CROSS-REFERENCE TO RELATED APPLICATIONS

This application is a continuation-in-part of a copendiing U.S. Ser. No. 503,705, filed Sept. 6, 1974, now U.S. Pat. No. 4,153,693.

BACKGROUND OF THE INVENTION

This invention relates to a novel pyridone-acetic acid derivative and to the use thereof as an intermediate in the process for the preparation of certain cephem derivaties which have excellent antibacterial activity.

SUMARY OF THE INVENTION

According to the present invention, there is provided the novel compound, 3,5-dichloro-4-pyridone-1-acetic acid (I).

DETAILED DISCUSSION

The acid (I) (m.p. 240° C.) can be prepared in the same way as known similar compounds by methods generally known in the art. Thus, it can be obtained from 3,5-dichloro-4-pyridone by reacting the latter with chloroacetic acid or bromoacetic acid, for example in a manner similar to that described in *Liebigs Annalen der Chemie und Pharmazie,* volume 494 (1932), page 294.

The acid (I) is a valuable intermediate for the preparation of certain cephem derivatives which are described and claimed in British application No. 38833/74 and in United States application Ser. No. 503,705, now U.S. Pat. No. 4,153,693. For example, the acid (I) can be reacted with 7-aminocephalosporanic acid to yield 7-(3,5-dichloro-1,4-dihydro-4-oxo-1-pyridylacetamido)—cephalosporanic acid (as described below in Example 2), which compound has excellent antibacterial activity against gram-negative and gram-positive bacteria.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 9.5 g of chloroacetic acid in 25 ml of water is neutralized with sodium carbonate and is then added to a warm solution of 16.4 g of 3,5-dichloro-4-pyridone in 100 ml of normal sodium hydroxide solution. After refluxing for three hours, the mixture is acidified with hydrochloric acid and the resulting 3,5-dichloro-4-pyridone-1-acetic acid is recrystallized from dilute ethanol. M.p. 240°.

EXAMPLE 2

0.224 ml of trichloroacetyl chloride is added to 443 mg of 3,5-dichloro-4-pyridone-1-acetic acid in 10 ml of absolute dimethyl formamide with ice cooling. After stirring for 30 minutes, a solution of 554 mg of 7-aminocephalosporanic acid and 1 g of N-trimethyl-silylacetamide in 5 ml off dimethyl formamide is added. The mixture is stirred for a further 30 minutes with ice cooling and is then pored into water and the pH adjusted to 5. After washing with ether, the pH is adjusted to 2 and the mixture is extraced with ethyl acetate. The extract is dried and evaporated, and the residue is crystallised by means of ether to give 7-(3,5-dichloro-1,4-dihydro-4-oxo-1-pyridylacetamido)-cephalosporanic acid. Infrared spectrum (in K Br): 1760, 1730, 1700, 1670, 1600, 1390, 1220 $cm^{-1}$.

EXAMPLE 3

In analogy to Example 2, from 3,5-dichloro-4-pyridone-1-acetic acid and 3-(5-methyl-1,3,4-thiadiazolyl-2-mercaptomethyl)-7-amino-3-cephem-4-carboxylic acid, there is obtained 3-(5-methyl-1,3,4-thiadiazolyl-2-mercaptomethyl)-7-(3,5-dichloro-1,4-dihydro-4-oxo-1-pyridyl-acetamido)-3-cephem-4-carboxylic acid. Infrared spectrum (in KBr): 1770, 1690, 1640, 1590, 1380 and 1220 $cm^{-1}$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. 3,5-Dichloro-4-pyridone-1-acetic acid.

* * * * *